United States Patent
Sekimoto (10) Patent No.: US 10,094,763 B2
(45) Date of Patent: Oct. 9, 2018

(54) MICROVIABLE PARTICLE COUNTING SYSTEM AND MICROVIABLE PARTICLE COUNTING METHOD

(71) Applicant: RION Co., Ltd., Tokyo (JP)

(72) Inventor: Kazuma Sekimoto, Tokyo (JP)

(73) Assignee: RION Co., Ltd., Tokyo (JP)

( * ) Notice: Subject to any disclaimer, the term of this patent is extended or adjusted under 35 U.S.C. 154(b) by 0 days.

(21) Appl. No.: 15/681,000

(22) Filed: Aug. 18, 2017

(65) Prior Publication Data

US 2018/0058998 A1     Mar. 1, 2018

(30) Foreign Application Priority Data

Aug. 26, 2016   (JP) .................................. 2016-166325

(51) Int. Cl.
| | |
|---|---|
| *G01N 21/00* | (2006.01) |
| *G01N 15/14* | (2006.01) |
| *G01N 21/64* | (2006.01) |
| *G01N 15/00* | (2006.01) |

(52) U.S. Cl.
CPC ....... *G01N 15/147* (2013.01); *G01N 15/1459* (2013.01); *G01N 15/1475* (2013.01); *G01N 21/6428* (2013.01); *G01N 2015/0088* (2013.01); *G01N 2015/1486* (2013.01)

(58) Field of Classification Search
CPC ........ G01N 21/29; G01N 33/32; G01N 21/05; G01N 21/293; G01N 33/2888
USPC ......................................................... 356/441
See application file for complete search history.

(56) References Cited

U.S. PATENT DOCUMENTS

| | | | |
|---|---|---|---|
| 2012/0178846 A1* | 7/2012 | Sun ......................... | C08J 3/247 |
| | | | 522/161 |
| 2014/0335557 A1 | 11/2014 | Ichijyo | |
| 2015/0346077 A1 | 12/2015 | Sekimoto | |
| 2016/0193393 A1* | 7/2016 | Peatfield ............. | A61M 1/0033 |
| | | | 604/319 |
| 2017/0055369 A1* | 2/2017 | Woolard ............... | H01L 23/473 |

FOREIGN PATENT DOCUMENTS

| | | |
|---|---|---|
| JP | 2008264668 A2 | 11/2008 |
| JP | 2013117466 A2 | 6/2013 |
| JP | 2014039890 A2 | 3/2014 |

(Continued)

OTHER PUBLICATIONS

Japanese Office Action dated Feb. 9, 2017 for the corresponding Japanese Patent Application No. 2016-166325 and its partial English translation.

(Continued)

*Primary Examiner* — Md M Rahman
(74) *Attorney, Agent, or Firm* — Rankin, Hill & Clark LLP (57) ABSTRACT

A microviable particle counting system includes: a microviable particle counting instrument configured to detect autofluorescence of a microviable particle in a sample as fluid, thereby counting the microviable particle in the sample; and a former-stage irradiator provided at a former stage of the microviable particle counting instrument to irradiate the sample with ultraviolet light. The ultraviolet light contains first ultraviolet light having such a wavelength that a carbon-carbon covalent bond is disconnected, and the first ultraviolet light has a wavelength shorter than 200 nm.

14 Claims, 4 Drawing Sheets

(56) References Cited

FOREIGN PATENT DOCUMENTS

| JP | 2014153199 A2 | 8/2014 |
| JP | 2016040533 A2 | 3/2016 |
| JP | 2016040534 A2 | 3/2016 |

OTHER PUBLICATIONS

Anonymous: "UV Low-pressure lamps", Jan. 1, 2011, XP055442434, Retrieved from the Internet: URL: https://www.heraeus.com/en/hng/products_and_solutions/uv_lamps_and_systems/uv_low_pressure_lamps.aspx [retrieved on Jan. 18, 2018]; section "UV Low-pressure lamps"; Cited in European search report and EP Office action.

European search report dated Feb. 8, 2018 in the corresponding European Patent Application No. 17 187 263.3.

EP Office action dated Feb. 23, 2018 in the corresponding European Patent Application No. 17 187 263.3.

* cited by examiner

MICROVIABLE PARTICLE COUNTING SYSTEM AND MICROVIABLE PARTICLE COUNTING METHOD

CROSS-REFERENCE TO RELATED APPLICATION

This application claims priority from Japanese Patent Application No. 2016-166325 filed with the Japan Patent Office on Aug. 26, 2016, the entire content of which is hereby incorporated by reference.

BACKGROUND

1. Technical Field

The present disclosure relates to a microviable particle counting system and a microviable particle counting method.

2. Description of the Related Art

A sample such as mineral water might contain bacteria such as heterotrophic bacteria. For this reason, the bacteria are cultivated in agar, and the degree of mixing of such bacteria is measured. However, in this method, it takes considerable days (e.g., one to two weeks) to obtain a measurement result. Thus, it has been demanded that the degree of mixing of bacteria etc. can be specified within a short period of time or in real time in a manufacturing line.

In view of such a demand, a certain microviable particle counting instrument is configured to measure microviable particles such as bacteria in real time based on autofluorescence emitted from the microviable particles (see, e.g., JP-A-2013-117466). Moreover, a certain microviable particle counting instrument is configured such that the intensity of autofluorescence of microviable particles is increased by irradiation of a sample with ultraviolet light within a UV-C wavelength range at former processing of microviable particle counting (see, e.g., JP-A-2014-153199).

SUMMARY

A microviable particle counting system includes a microviable particle counting instrument configured to detect autofluorescence of microviable particles in a sample as fluid, thereby counting the microviable particles in the sample, and a former-stage irradiator provided at a former stage of the microviable particle counting instrument to irradiate the sample with ultraviolet light containing an ozone generation beam.

DESCRIPTION OF THE EMBODIMENTS

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

However, the sample such as mineral water might contain, as a mixed substance, an organic substance (e.g., a humic substance such as humic acid or fulvic acid) emitting fluorescence leading to background noise on the autofluorescence of the microviable particles. In this case, due to such fluorescence of the organic substance, it is difficult to detect weak autofluorescence of the bacteria targeted for measurement, leading to the probability that a counting error is caused.

One objective of the present disclosure is to provide a microviable particle counting system and a microviable particle counting method configured so that microviable particles can be accurately counted within a short period of time or in real time even in a case where a mixed organic substance emitting fluorescence leading to background noise on autofluorescence of the microviable particles is contained in a sample.

A microviable particle counting system (this system) according to one aspect of the present disclosure includes a microviable particle counting instrument configured to detect autofluorescence of microviable particles in a sample as fluid, thereby counting the microviable particles in the sample, and a former-stage irradiator provided at a former stage of the microviable particle counting instrument to irradiate the sample with ultraviolet light. The ultraviolet light contains first ultraviolet light having such a wavelength that a carbon-carbon covalent bond is disconnected, and the first ultraviolet light has a wavelength shorter than 200 nm.

In this system, the former-stage irradiator may include a single light source configured to irradiate the sample with the ultraviolet light containing the first ultraviolet light and second ultraviolet light having a wavelength longer than that of the first ultraviolet light within a UV-C wavelength range.

In this system, the former-stage irradiator may irradiate the sample with the ultraviolet light without performing aeration for the sample by means of air irradiated with the ultraviolet light.

In this system, the former-stage irradiator may include a storage configured to store the sample, the light source configured to irradiate the sample in the storage with the ultraviolet light, and a flow passage portion configured to supply the sample in the storage to the microviable particle counting instrument. In this case, the light source may include a light emitter configured to emit the ultraviolet light, and may irradiate the sample with the ultraviolet light in a state in which the entirety of the light emitter is submerged in the sample in the storage.

In this system, the former-stage irradiator may include the light source configured to emit the ultraviolet light, a flow passage portion disposed at the periphery of the light source such that the sample circulates in the flow passage portion, and a shield configured to cover the light source and the flow passage portion to reflect or absorb the ultraviolet light.

In this case, the light source may include a light emitter configured to emit the ultraviolet light, and the flow passage portion is a U-shaped tube extending along the periphery of the light emitter.

Alternatively, the light source may include a light emitter configured to emit the ultraviolet light. The flow passage portion may be a cylindrical case, and may be configured to house the light source along a center axis inside the flow passage portion. A sample outlet port may be, at the flow passage portion, provided at a position identical to or higher than an upper end of the light emitter above a sample inlet port of the flow passage portion.

In this case, the inlet port and the outlet port may be provided along a tangential direction of an outer peripheral surface of the flow passage portion.

In this system, the sample may be water, and the microviable particles may contain at least one of riboflavin or NAD(P)H.

A microviable particle counting method according to another aspect of the present disclosure includes irradiating a sample as fluid with ultraviolet light, and detecting autofluorescence of microviable particles in the sample irradiated with the ultraviolet light, thereby counting the microviable particles in the sample. The ultraviolet light contains first ultraviolet light having such a wavelength that a carbon-carbon covalent bond is disconnected, and the first ultraviolet light has a wavelength shorter than 200 nm.

According to the microviable particle counting system and the microviable particle counting method according to the above-mentioned aspects of the present disclosure, the microviable particles can be accurately counted in real time even in the case where the mixed organic substance emitting the fluorescence leading to the background noise on the autofluorescence of the microviable particles is contained in the sample.

Embodiments of the present disclosure will be described below with reference to drawings.

First Embodiment

Figure 1:
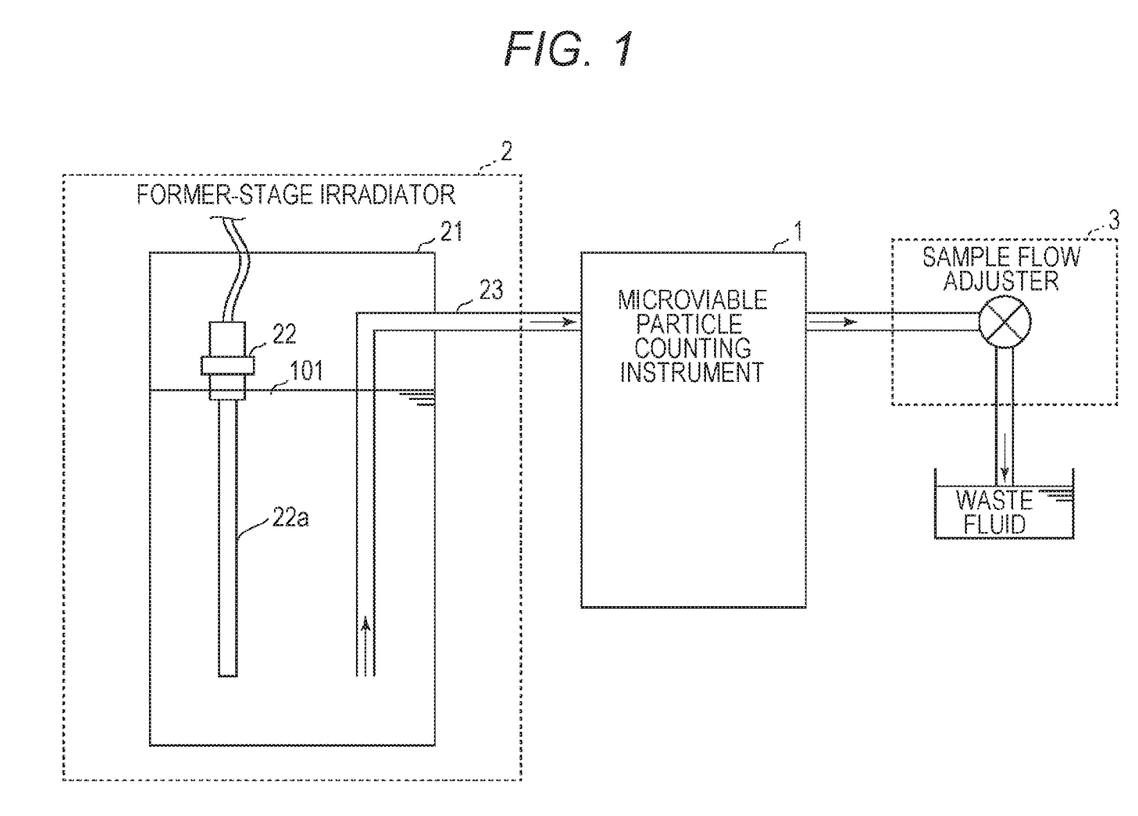
FIG. 1 is a block diagram of a structure of a microviable particle counting system of a first embodiment of the present disclosure.

FIG. 1 is a block diagram of a structure of a microviable particle counting system of a first embodiment of the present disclosure. The microviable particle counting system of the first embodiment includes a microviable particle counting instrument 1, a former-stage irradiator 2, and a sample flow adjuster 3.

The microviable particle counting instrument 1 is configured to detect autofluorescence of microviable particles in a sample as fluid, thereby counting the microviable particles in the sample. That is, the microviable particle counting instrument 1 irradiates the sample with measurement light (excitation light) to detect the autofluorescence of the microviable particles in the sample (sample fluid), thereby counting the microviable particles in the sample. For example, a microviable particle counting instrument described in JP-A-2013-117466 or JP-A-2014-153199 can be used as the microviable particle counting instrument 1. The microviable particle counting instrument 1 can count microviable particles with a size of 0.1 μm to hundreds of μm, for example. Specifically, the microviable particles targeted for counting are bacteria, yeast, and fungus, for example. Cells of the microviable particles contain a particular substance (e.g., riboflavin and NAD(P)H: nicotinamide adenine dinucleotide (phosphate)) required for metabolism and emitting the autofluorescence, for example. Thus, the microviable particles can be counted by detection of the autofluorescence.

Figure 2:
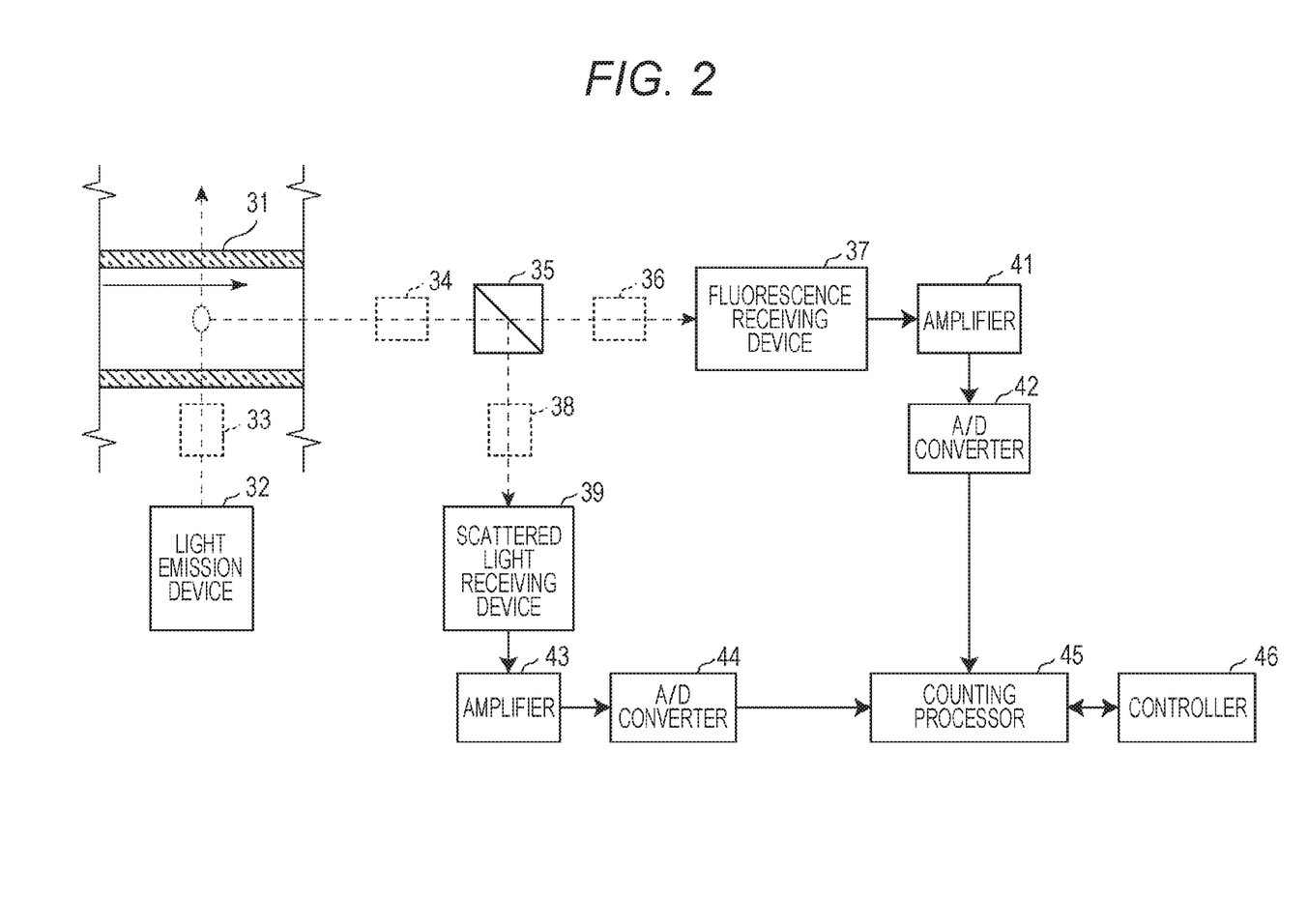
FIG. 2 is a block diagram of a structure of a microviable particle counting instrument of FIG. 1.

FIG. 2 is a block diagram of a structure of the microviable particle counting instrument 1 of FIG. 1. As illustrated in FIG. 2, the microviable particle counting instrument 1 includes a flow cell 31, a light emission device 32, an irradiation optical system 33, a detection optical system 34, a scattered light selection optical element 35, a light receiving optical system 36, a fluorescence receiving device 37, a light receiving optical system 38, and a scattered light receiving device 39.

The flow cell 31 forms a flow passage of the sample containing the microviable particles targeted for counting. The flow cell 31 is a transparent tubular member forming the flow passage. The flow cell 31 is made of synthetic silica or sapphire, for example. The flow cell 31 has a hollow quadrangular prism shape, for example.

The light emission device 32 includes a light source (e.g., a laser diode semiconductor light emission element) configured to emit light (laser light in this embodiment) with a predetermined wavelength. Such a light source emits the measurement light (the excitation light) for exciting the autofluorescent substance of the microviable particles. Such measurement light has a wavelength specific to the autofluorescent substance within a range from an ultraviolet light region to a green visible light region, for example.

For example, a wavelength corresponding to a peak of an excitation absorption spectrum of NAD(P)H is about 340 nm. A wavelength corresponding to a peak of an excitation absorption spectrum of riboflavin is about 375 nm and about 450 nm. Thus, laser light (e.g., laser light with a wavelength of 405 nm) with a wavelength within a range of 330 nm to 500 nm is used as the measurement light (the excitation light) for riboflavin, for example.

The irradiation optical system 33 is configured to irradiate the sample flowing in the flow passage of the flow cell 31 with the measurement light (the excitation light) from a direction (in this embodiment, a vertical direction against a traveling direction of the sample) different from the sample traveling direction in the flow passage. The irradiation optical system 33 includes, for example, various kinds of lenses (e.g., a collimator lens, a biconvex lens, and a cylindrical lens). For example, the irradiation optical system 33 adjusts the laser light from the light emission device 32 to a parallel beam, and irradiates the sample in the flow passage with such a parallel beam as the measurement light. The sample flowing in the flow passage of the flow cell 31 is irradiated with such measurement light, and therefore, a detection region is formed. Note that a beam damper (a beam trap) configured to shield the measurement light having transmitted through the flow cell 31 may be disposed.

The detection optical system 34 is configured to cause scattered light and autofluorescence to enter a predetermined incidence plane of the scattered light selection optical element 35, the scattered light and the autofluorescence being emitted from the particles in the flow passage by irradiation with the measurement light as mentioned above. For example, a condensing lens or the following optical system may be used as the detection optical system 34. Such an optical system has a pinhole for shielding background light and a condensing lens disposed on each of front and back sides of the pinhole.

In the case of irradiating the microviable particles with the measurement light, the scattered light and the autofluorescence from the microviable particles enter the predetermined incidence plane of the scattered light selection optical element 35. The sample might contain an organic substance (hereinafter referred to as a "mixed organic substance") emitting fluorescence leading to background noise on the autofluorescence of the microviable particles targeted for counting. In this case, when the mixed organic substance is irradiated with the measurement light, such a mixed organic substance also emits the fluorescence.

For example, a wavelength corresponding to a peak of an autofluorescence spectrum of riboflavin is about 520 nm. The scattered light from the particles has the same wavelength as that of the measurement light. For example, in a case where the measurement light (i.e., the excitation light of riboflavin) has a wavelength of 405 nm, the scattered light from the particles also has a wavelength of 405 nm. Note that the wavelength corresponding to the peak of the excitation or fluorescence spectrum will be referred to as a "peak wavelength."

A humic substance such as humic acid or fulvic acid might be contained as the mixed organic substance in the sample as fluid. In this case, an excitation/fluorescence spectrum of the humic substance shows such broad characteristics that a peak wavelength thereof is about 320 nm/430 nm (excitation/fluorescence) and about 440 nm/510 nm (excitation/fluorescence). Thus, such a mixed organic substance emits fluorescence with a wavelength of around 520 nm in the case of a measurement light wavelength of 405 nm, for example. Thus, the fluorescence from the mixed organic substance leads to the background noise on the autofluorescence from riboflavin.

Note that in a case where the sample is water in a liquid form, Raman scattered light from the water irradiated with the measurement light also enters the scattered light selection optical element 35 through the detection optical system 34. For example, in a case where the measurement light has a wavelength of 405 nm, the peak wavelength of the Raman scattered light from the water is about 465 nm.

Moreover, in this embodiment, the measurement light enters the flow passage of the flow cell 31 in a direction different from the optical axis of the detection optical system 34. Thus, scattered light resulted from side scattering enters the scattered light selection optical element 35 by the detection optical system 34.

The scattered light selection optical element 35 is an optical element (e.g., a dichroic mirror) configured to allow transmission of light with a wavelength within the wavelength range of the autofluorescence from the particles while reflecting light with a wavelength within the wavelength range (i.e., the wavelength range of the measurement light) of the scattered light from the particles.

The light receiving optical system 36 is configured to condense light (the autofluorescence) to the fluorescence receiving device 37 by a condensing lens group, the light having been transmitted through the scattered light selection optical element 35. Note that the light receiving optical system 36 may have a long-path filter. This long-path filter is, for example, configured to shield the Raman scattered light according to the intensity of the Raman scattered light having transmitted through the scattered light selection optical element 35 and to allow transmission of light with a wavelength within the wavelength range of the autofluorescence. The fluorescence receiving device 37 has a semiconductor light receiving element such as a photodiode or a phototransistor or a photomultiplier tube. The fluorescence receiving device 37 receives the condensed light with the semiconductor light receiving element or the photomultiplier tube, thereby converting the received light into an electric signal. Then, the fluorescence receiving device 37 outputs the electric signal with a voltage corresponding to a received light amount.

The light receiving optical system 38 is configured to condense light (the scattered light) to the scattered light receiving device 39 by the condensing lens group, the light having being reflected by the scattered light selection optical element 35. The scattered light receiving device 39 has a semiconductor light receiving element such as a photodiode or a phototransistor or a photomultiplier tube. The scattered light receiving device 39 receives the condensed scattered light with the semiconductor light receiving element or the photomultiplier tube, thereby converting the received scattered light into an electric signal. Then, the scattered light receiving device 39 outputs the electric signal with a voltage corresponding to a received light amount.

Further, the microviable particle counting instrument 1 includes an amplifier 41, an A/D converter 42, an amplifier 43, an A/D converter 44, a counting processor 45, and a controller 46. The amplifier 41 is configured to amplify, with a predetermined amplification factor, the voltage of the electric signal from the fluorescence receiving device 37. The A/D converter 42 is configured to convert, into a digital signal, the electric signal with the amplified voltage. The amplifier 43 is configured to amplify, with a predetermined amplification factor, the voltage of the electric signal from the scattered light receiving device 39. The A/D converter 44 is configured to convert, into a digital signal, the electric signal with the amplified voltage.

The counting processor 45 is a digital processing circuit. The counting processor 45 is configured to count microviable particles passing through a measurement region (e.g., for each particle size classification) based on the digital signal corresponding to the autofluorescence from the A/D converter 42 and the digital signal corresponding to the scattered light from the A/D converter 44. Specifically, the counting processor 45 obtains the waveform of the signal corresponding to the autofluorescence and the waveform of the signal corresponding to the scattered light. In a case where the pulse height values of these two signals each exceed a threshold, the counting processor 45 determines that a single microviable particle has been detected, and then, performs counting. Note that in a case where only the signal corresponding to the scattered light from the A/D converter 44 among these two signals exceeds the threshold, the counting processor 45 determines that a single non-microviable particle has been detected. The controller 46 is configured to control an internal device such as the counting processor 45 to obtain a measurement result from the counting processor 45. For example, the controller 46 may output the obtained measurement result as measurement data. Alternatively, the controller 46 may create a graph or a drawing based on the measurement result, thereby displaying the graph or the drawing on a display device (not shown).

Referring back to FIG. 1, the former-stage irradiator 2 is provided at a former stage of the microviable particle counting instrument 1 to irradiate, with ultraviolet light, the sample as fluid flowing into the microviable particle counting instrument 1. For example, in a case where the sample is mineral water, the sample might contain, as mentioned above, the mixed organic substance emitting the fluorescence leading to the background noise on the autofluorescence of the microviable particles targeted for counting. For this reason, the former-stage irradiator 2 is configured to decompose the mixed organic substance in such a manner that the sample is irradiated with ultraviolet light containing an ozone generation beam. This ozone generation beam has a wavelength of equal to or less than 240 nm (e.g., 185 nm) so that an oxygen molecular bond is disconnected. For example, the former-stage irradiator 2 irradiates, using a light source such as an ozone lamp configured to emit light with a wavelength of 185 nm or an excimer lamp configured to emit light with a peak wavelength of 172 nm, the sample with the ultraviolet light containing the ozone generation beam.

In this embodiment, the former-stage irradiator 2 irradiates, using a single light source lamp, the sample with ultraviolet light containing the above-mentioned ozone generation beam and a sterilization beam. This sterilization beam has a wavelength (e.g., 254 nm) longer than that of the ozone generation beam within a UV-C wavelength range (200 nm to 280 nm). By this sterilization beam, ozone generated by the above-mentioned ozone generation beam is decomposed, and the intensity of the autofluorescence of riboflavin contained in the microviable particles of the sample increases.

In this embodiment, the sample is water (i.e., liquid) such as mineral water (hereinafter also referred to as "sample water"). The microviable particles targeted for counting contain at least either one of riboflavin or NAD(P)H. The above-mentioned mixed organic substance contains at least either one of humic acid or fulvic acid. The former-stage irradiator 2 irradiates the sample water with the ozone generation beam with such a wavelength (equal to or less than about 200 nm, and 185 nm in this embodiment) that a carbon-carbon covalent bond is disconnected. Using the ozone generation beam with such a wavelength that a carbon-carbon covalent bond is disconnected, the mixed organic substance is effectively decomposed.

Note that in this embodiment, the former-stage irradiator 2 decomposes the mixed organic substance by irradiation of the sample water with the above-mentioned ultraviolet light without performing aeration for the sample by means of air (i.e., air containing ozone) irradiated with the ultraviolet light. Thus, the microviable particle counting instrument 1 can perform counting without influence of air bubbles due to aeration.

The microviable particle counting system of the first embodiment is a batch-type counting system. As illustrated in FIG. 1, the former-stage irradiator 2 includes a storage 21 having a container configured to store sample water 101, a light source 22, and a flow passage portion 23. The light source 22 is configured to irradiate the sample water 101 in the storage 21 with the above-mentioned ultraviolet light. The flow passage portion 23 is configured to supply the sample water 101 as fluid in the storage 21 to the microviable particle counting instrument 1.

Note that in a case where the storage 21 is made of a material through which the ultraviolet light from the light source 22 is transmitted, a shielding material configured to shield the ultraviolet light may be disposed at the outer periphery of the storage 21 to reduce leakage of the ultraviolet light from the light source 22 to the outside. It is to be desired that a material reflecting the ultraviolet light, such as aluminum and polytetrafluoroethylene (PTFE), is used as the shielding material.

The light source 22 has a light emitter 22a configured to emit the above-mentioned ultraviolet light. By discharging inside the light emitter 22a, the ozone generation beam and the sterilization beam are emitted from the light emitter 22a. In this embodiment, the wavelength of the ozone generation beam is 185 nm, and the wavelength of the sterilization beam is 254 nm.

Moreover, the light source 22 is disposed inside the container of the storage 21. The light source 22 irradiates the sample water 101 with the above-mentioned ultraviolet light in a state in which the entirety of the light emitter 22a is submerged in the sample water 101 in the storage 21. With this structure, ozone generation in external air due to the ozone generation beam from the light source 22 is reduced. Note that as long as measurement can be performed without influence of ozone generation in external air around the light emitter 22a, the light emitter 22a is not necessarily submerged in the sample water 101.

Note that an agitation device configured to agitate the sample may be provided at the former-stage irradiator 2 such that the sample water 101 in the storage 21 is equally irradiated with the ultraviolet light.

The sample flow adjuster 3 has a pump and/or a valve, for example. The sample flow adjuster 3 is configured to adjust the flow rate of the sample (i.e., the sample flowing into the microviable particle counting instrument 1) flowing out of the microviable particle counting instrument 1. Further, the sample flow adjuster 3 is configured to discharge the sample water for which counting by the microviable particle counting instrument 1 has been completed.

Next, counting of the microviable particles in the microviable particle counting system of the first embodiment will be described.

The microviable particle counting system of the first embodiment employs a batch technique. Thus, as illustrated in FIG. 1, a certain amount of sample water 101 enters the storage 21 per measurement such that the light emitter 22a of the light source 22 is covered with the sample water 101. In this embodiment, the sample water 101 is water such as mineral water or tap water.

Next, the light source 22 is turned on to irradiate the sample water 101 with the above-mentioned ultraviolet light. Thus, the sample water 101 is irradiated with the above-mentioned ozone generation beam and the above-mentioned sterilization beam for a predetermined period of time. For example, a period of time of irradiation with the above-mentioned ozone generation beam emitted from the light emitter 22a with an output power of 0.17 W may be approximately 2 minutes or more. Also, for example, a period of time of irradiation with the above-mentioned sterilization beam emitted from the light emitter 22a with an output power of 1.7 W may be approximately 2 minutes or more. Note that at this point, no aeration is performed for the sample water 101.

By this ozone generation beam, dissolved oxygen in the sample water 101 is changed into ozone, and the mixed organic substance such as humic acid or fulvic acid is decomposed. Moreover, by this sterilization beam, the ozone in the sample water 101 is decomposed into radical. By the generated radical, the mixed organic substance is also decomposed.

This decreases the concentration of the mixed organic substance in the sample water 101. Moreover, by the above-mentioned sterilization beam, the intensity of the autofluorescence of riboflavin in the microviable particles increases.

After the sample water 101 has been irradiated with the above-mentioned ozone generation beam and the above-mentioned sterilization beam for the predetermined period of time, the light source 22 is turned off. Subsequently, the sample flow adjuster 3 causes the sample water 101 to flow into the microviable particle counting instrument 1, and the microviable particle counting instrument 1 begins counting the microviable particles.

The microviable particle counting instrument 1 counts the microviable particles in the sample water 101 as fluid. At this point, the mixed organic substance is decomposed by the above-mentioned ozone generation beam in former processing. Thus, the intensity of the fluorescence leading to the background noise is lower than the intensity of the autofluorescence of the microviable particles. As a result, the microviable particles in the sample water 101 are counted with a high accuracy.

As mentioned above, according to the first embodiment, the microviable particle counting instrument 1 detects the autofluorescence of the microviable particles in the sample water 101 as the sample fluid, thereby counting the microviable particles in the sample water 101. The former-stage irradiator 2 configured to irradiate the sample water 101 with the ultraviolet light is provided at the former stage of the microviable particle counting instrument 1. The sample water 101 contains the mixed organic substance emitting the fluorescence leading to the background noise on the autofluorescence of the microviable particles. The former-stage irradiator 2 decomposes the mixed organic substance in the sample water 101 in such a manner that the sample water 101 is irradiated with the ultraviolet light containing the ozone generation beam.

With this structure, even when the sample water 101 contains the mixed organic substance emitting the fluorescence leading to the background noise on the autofluorescence of the microviable particles targeted for counting, the mixed organic substance is decomposed by the former-stage irradiator 2. Thus, the microviable particles are accurately counted within a short period of time (i.e., without cultivation of bacteria for a long period of time) by the batch technique. Note that it has been confirmed, by experiment, that the above-mentioned ozone generation beam does not influence a microviable particle counting result.

Second Embodiment

Figure 3:
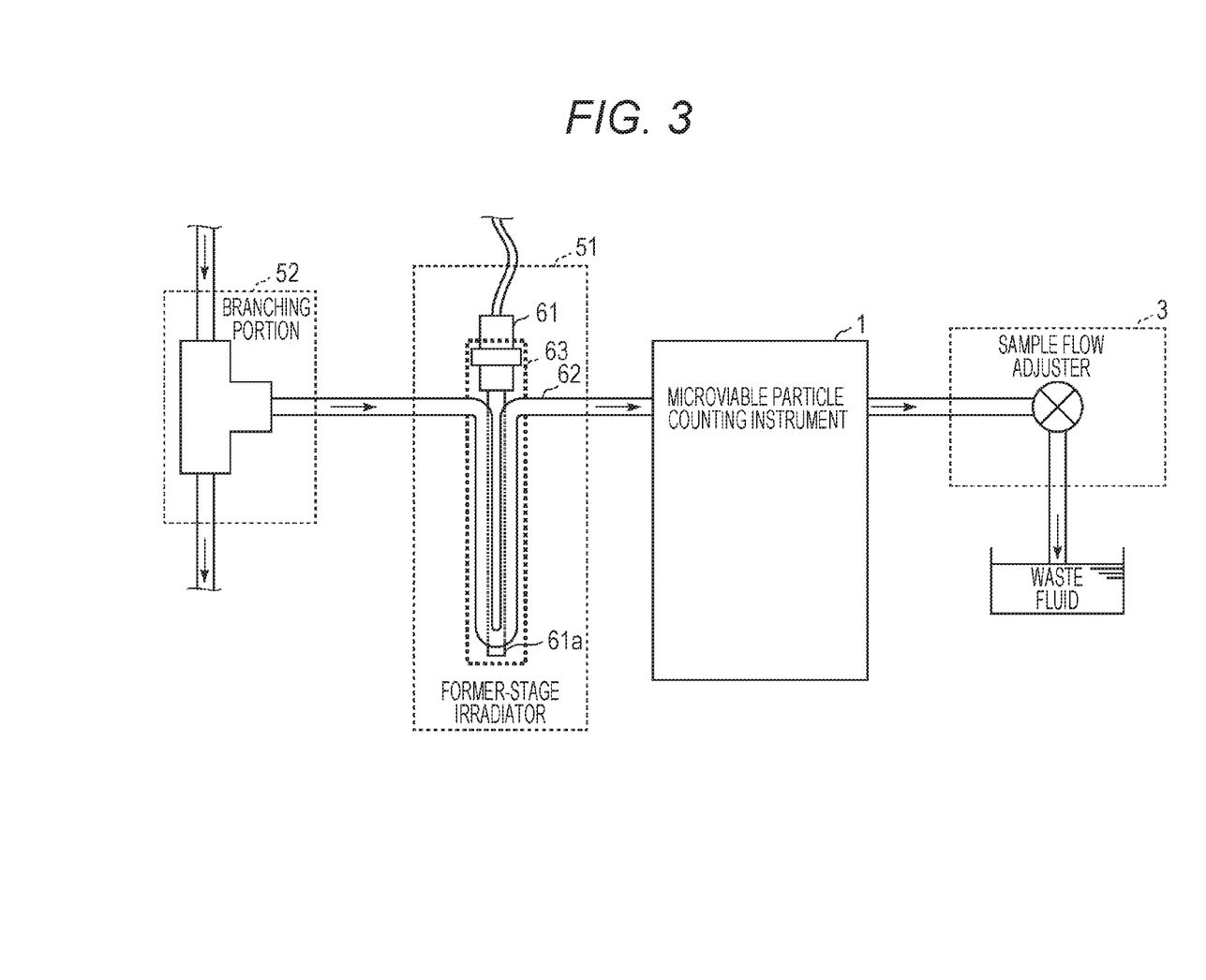
FIG. 3 is a block diagram of a structure of a microviable particle counting system of a second embodiment of the present disclosure.

FIG. 3 is a block diagram of a structure of a microviable particle counting system of a second embodiment of the present disclosure. The microviable particle counting system of the second embodiment is a continuous counting system. Thus, the microviable particle counting system of the second embodiment includes a former-stage irradiator 51 for a continuous technique. In the second embodiment, a microviable particle counting instrument 1 is configured to continuously count microviable particles in a sample (sample fluid) as fluid. At a stage before the sample fluid flows into the microviable particle counting instrument 1, the former-stage irradiator 51 irradiates the sample fluid with an ozone generation beam and a sterilization beam as mentioned above.

The former-stage irradiator 51 in the second embodiment includes a light source 61 configured to emit ultraviolet light, a flow passage portion 62, and a shield 63. The flow passage portion 62 is disposed at the periphery of the light source 61. The sample fluid circulates in the flow passage portion 62. The shield 63 is configured to cover the light source 61 and the flow passage portion 62 (the outer peripheries of the light source 61 and the flow passage portion 62) to reflect or absorb the ultraviolet light.

The light source 61 is similar to the light source 22 of the first embodiment, and has a light emitter 61a. In the second embodiment, the flow passage portion 62 is formed of a silica tube, and has a tubular shape, for example. The flow passage portion 62 has a U-shaped flow passage portion extending along the light emitter 61a of the light source 61. That is, the flow passage portion 62 is a U-shaped tube extending along the periphery of the light emitter 61a (extending to sandwich the light emitter 61a).

The shield 63 is made of a material reflecting the ultraviolet light, such as aluminum and polytetrafluoroethylene (PTFE). Since the outer peripheries of the light source 61 and the flow passage portion 62 are covered with the shield 63, the ultraviolet light from the light source 61 less leaks to the outside, and the flow passage portion 62 is efficiently irradiated with such ultraviolet light. Note that the shield 63 may be a case configured to house the light source 61 and the flow passage portion 62. Alternatively, the shield 63 may be configured to cover the outer periphery of the case housing the light source 61 and the flow passage portion 62.

Note that ozone is generated when air (external air) around the light source 61 is irradiated with the ultraviolet light from the light source 61. Thus, it is to be desired that the shield 63 is foil-like and is disposed in close contact with the light source 61 and the flow passage portion 62 such that a space between the shield 63 and each of the light source 61 and the flow passage portion 62 is small. Moreover, a joint portion between the shield 63 and the light source 61 and a joint portion between the shield 63 and the flow passage portion 62 may be hermetically closed to suppress the ozone generated inside the shield 63 from leaking to the outside.

Next, counting of the microviable particles in the microviable particle counting system of the second embodiment will be described.

The microviable particle counting system of the second embodiment employs the continuous technique. Thus, while the sample fluid is circulating, ultraviolet light irradiation by the former-stage irradiator 51 and counting of the microviable particles by the microviable particle counting instrument 1 are continuously performed. In this embodiment, the sample fluid is water (sample water) such as mineral water or tap water.

First, by the sample flow adjuster 3, the sample water is branched from a main flow passage (e.g., a tap water pipe) at a branching portion 52, and then, flows into the former-stage irradiator 51. Meanwhile, the light source 61 is turned on, and the sample water is irradiated with the above-mentioned ultraviolet light during a period for which the sample water is flowing through the flow passage portion 62. Thus, the sample water is irradiated with the above-mentioned ozone generation beam and the above-mentioned sterilization beam for a predetermined period of time according to the flow velocity of the sample water and the length of the flow passage portion 62. Note that at this point, no aeration is performed for the sample water.

This decreases the concentration of a mixed organic substance in the sample water as in the first embodiment. Moreover, the intensity of autofluorescence of riboflavin in the microviable particles is increased by the above-mentioned sterilization beam.

Then, after circulated in the flow passage portion 62 of the former-stage irradiator 51 and irradiated with the above-mentioned ozone generation beam and the above-mentioned sterilization beam for the predetermined period of time, the sample water flows into the microviable particle counting instrument 1.

The microviable particle counting instrument 1 counts the microviable particles in the sample water. At this point, the mixed organic substance is decomposed by the above-mentioned ozone generation beam in former processing. Thus, the intensity of fluorescence leading to background noise is lower than the intensity of the autofluorescence of the microviable particles. As a result, the microviable particles in the sample water are accurately counted.

Note that structures and operation of other components in the microviable particle counting system of the second embodiment are similar to those of the first embodiment, and therefore, description thereof will not be repeated.

Note that in the second embodiment, a sample flow adjuster 3 is not necessarily provided as long as the flow rate of the sample water circulating in the former-stage irradiator 51 and the microviable particle counting instrument 1 can be adjusted based on the water pressure of the main flow passage and/or a structure of the branching portion 52.

As mentioned above, according to the above-mentioned second embodiment, the former-stage irradiator 51 employing the continuous technique is provided at the former stage of the microviable particle counting instrument 1. The former-stage irradiator 51 irradiates the sample as fluid with the ultraviolet light containing the ozone generation beam. The sample might contain the mixed organic substance emitting the fluorescence leading to the background noise on the autofluorescence of the microviable particles.

With this structure, even when the sample contains the mixed organic substance emitting the fluorescence leading to the background noise on the autofluorescence of the microviable particles, the mixed organic substance is decomposed by the former-stage irradiator 51. Thus, the microviable particles are accurately counted in real time by the continuous technique.

Third Embodiment

A microviable particle counting system of a third embodiment of the present disclosure is a system including a former-stage irradiator 51 with a structure different from that of the microviable particle counting system of the second embodiment.

Figure 4A:
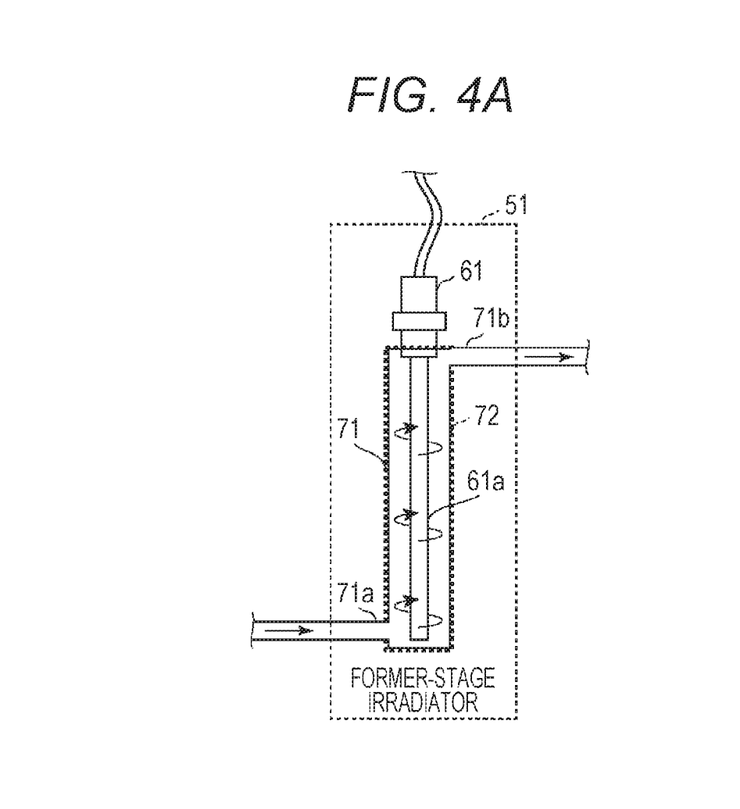
FIG. 4A is a side view of an example of a former-stage irradiator in a microviable particle counting system of a third embodiment of the present disclosure.
Figure 4B:
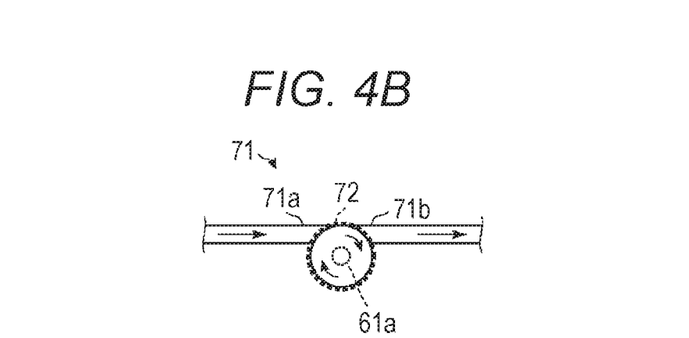
FIG. 4B is a bottom view of an example of a flow passage portion in the microviable particle counting system of the third embodiment of the present disclosure.

FIG. 4A is a side view of an example of the former-stage irradiator 51 in the microviable particle counting system of the third embodiment. FIG. 4B is a bottom view of an example of a flow passage portion 71 in the microviable particle counting system of the third embodiment.

The former-stage irradiator 51 of the third embodiment includes the flow passage portion 71 instead of the flow passage portion 62. The flow passage portion 71 is an upright cylindrical case, and is configured to house a light source 61 along a center axis inside the flow passage portion 71. That is, in the third embodiment, sample water flows into the flow passage portion 71 through a lower portion thereof, and circulates in contact with the light source 61. Then, the sample water flows out of the flow passage portion 71 through an upper portion thereof. Note that in the third embodiment, no aeration is also performed for the sample water as in other embodiments.

As illustrated in FIG. 4A, an inlet port 71a is provided at a predetermined height position near a bottom surface of the flow passage portion 71. An outlet port 71b is provided at a predetermined height position of the flow passage portion 71. The outlet port 71b is provided at a position higher than the inlet port 71a. That is, the outlet port 71b is provided at a position substantially identical to or higher than an upper end of a light emitter 61a above the inlet port 71a.

Moreover, as illustrated in FIG. 4B, the inlet port 71a and the outlet port 71b are provided along a tangential direction of an outer peripheral surface of the flow passage portion 71. That is, the inlet port 71a and the outlet port 71b are, along the tangential direction of the outer peripheral surface of the flow passage portion 71, provided respectively at predetermined positions radially apart from the center axis of the flow passage portion 71. With this structure, the sample water flowing in through the inlet port 71a spirally circulates at the periphery of the light emitter 61a of the light source 61, and then, flows out through the outlet port 71b.

In addition, a shield 72 configured to cover the outer peripheries of the light source 61 and the flow passage portion 71 to reflect or absorb ultraviolet light is placed on the outer peripheral surface of the flow passage portion 71. The shield 72 is made of a material similar to that of the shield 63.

Note that structures and operation of other components in the microviable particle counting system of the third embodiment are similar to those of the second embodiment, and therefore, description thereof will not be repeated.

Note that various changes and modifications to the above-mentioned embodiments are apparent to those skilled in the art. These changes and modifications may be made without departing from the gist and scope of the subject matter and impairing intended advantages. That is, it is intended that these changes and modifications are included in the scope of the claims.

For example, in the above-mentioned first to third embodiments, the sample is liquid including, e.g., drinking water such as mineral water. However, the sample may be gas (e.g., air).

Moreover, in the above-mentioned first to third embodiments, the light sources 22, 61 may be configured to emit the above-mentioned ozone generation beam without emitting the above-mentioned sterilization beam. In this case, when the autofluorescence of NAD(P)H is, for example, detected instead of riboflavin, the light emission device 32 and the irradiation optical system 33 of the microviable particle counting instrument 1 may be configured to irradiate, as the excitation light, the measurement light having a wavelength (e.g., about 350 nm) near the peak wavelength of the excitation absorption spectrum of NAD(P)H. The detection optical system 34, the scattered light selection optical element 35, the light receiving optical system 36, and the light receiving optical system 38 may be configured such that the autofluorescence with a peak wavelength of about 470 nm is detected at the fluorescence receiving device 37 and that the scattered light with the same wavelength as that of the measurement light is detected at the scattered light receiving device 39. Note that the humic substance has the above-mentioned excitation/fluorescence spectrum. Thus, even in the case of detecting the autofluorescence of NAD(P)H, the fluorescence emitted from such a mixed organic substance leads to the background noise on the autofluorescence from NAD(P)H. For this reason, the mixed organic substance is decomposed at the former-stage irradiator 2, 51, and therefore, the microviable particles can be accurately counted.

Further, in the above-mentioned first to third embodiments, humic acid and fulvic acid have been described as examples of the mixed organic substance. Other mixed organic substances may be contained in the sample.

In addition, in the above-mentioned first to third embodiments, the former-stage irradiator 2, 51 is provided as a body separated from the microviable particle counting instrument 1. The former-stage irradiator 2, 51 may be built in the microviable particle counting instrument 1.

The techniques of these embodiments are, for example, applicable to counting of microviable particles contained in a sample extracted from a nature, such as mineral water.

The embodiments of the present disclosure may be the following first to sixth aspects of a microviable particle counting system and a first aspect of a microviable particle counting method.

The first aspect of the microviable particle counting system includes a microviable particle counter configured to detect autofluorescence of microviable particles in fluid to count the microviable particles in the fluid, and a former-stage irradiator provided at a former stage of the microviable particle counter to irradiate the fluid as a sample with ultraviolet light. The sample contains a mixed organic substance emitting fluorescence leading to background noise on the autofluorescence of the microviable particles. The ultraviolet light contains an ozone generation beam. The former-stage irradiator irradiates the sample with the ultraviolet light, thereby decomposing the mixed organic substance in the sample.

The second aspect of the microviable particle counting system is the microviable particle counting system according to the first aspect, in which the former-stage irradiator irradiates, using a single light source, the sample with the ultraviolet light containing the ozone generation beam and a sterilization beam. The sterilization beam has any wavelength longer than that of the ozone generation beam within a UV-C wavelength range.

The third aspect of the microviable particle counting system is the microviable particle counting system according to the first aspect, in which the former-stage irradiator irradiates the sample with the ultraviolet light without performing aeration for the sample by means of air irradiated with the ultraviolet light.

The fourth aspect of the microviable particle counting system is the microviable particle counting system according to the first aspect, in which the former-stage irradiator includes a storage configured to store the sample, a light source configured to irradiate the sample in the storage with the ultraviolet light, and a flow passage portion configured to supply, as the fluid, the sample in the storage to the microviable particle counter. The light source includes a light emitter configured to emit the ultraviolet light. The sample is irradiated with the ultraviolet light in a state in which the entirety of the light emitter is submerged in the sample in the storage.

The fifth aspect of the microviable particle counting system is the microviable particle counting system according to the first aspect, in which the former-stage irradiator includes a light source configured to emit the ultraviolet light, a flow passage portion in which the sample circulates at the periphery of the light source, and a shield configured to cover the light source and the flow passage portion to reflect or absorb the ultraviolet light.

The sixth aspect of the microviable particle counting system is the microviable particle counting system according to any one of the first to fifth aspects, in which the sample is water, the microviable particles contain at least one of riboflavin or NAD(P)H, the mixed organic substance contains a humic substance, and the ozone generation beam has such a wavelength that a carbon-carbon covalent bond is disconnected.

The first aspect of the microviable particle counting method includes the step of irradiating a sample with ultraviolet light at a former stage of a microviable particle counter, and the step of causing the sample irradiated with the ultraviolet light to flow, as fluid, into the microviable particle counter, thereby detecting autofluorescence of microviable particles of the fluid to count the microviable particles of the fluid in the microviable particle counter. The sample contains a mixed organic substance emitting fluorescence leading to background noise on the autofluorescence of the microviable particles. The ultraviolet light contains an ozone generation beam. At the former stage of the microviable particle counter, the sample is irradiated with the ultraviolet light such that the mixed organic substance in the sample is decomposed.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:
1. A microviable particle counting system comprising:
a microviable particle counting instrument configured to detect autofluorescence of a microviable particle in a sample as fluid, thereby counting the microviable particle in the sample; and
a former-stage irradiator provided at a former stage of the microviable particle counting instrument to irradiate the sample with ultraviolet light,
wherein the sample includes a humic substance emitting fluorescence leading to background noise on the autofluorescence of the microviable particle,
the former-stage irradiator includes a single light source configured to irradiate the sample with the ultraviolet light containing first ultraviolet light and second ultraviolet light, the first ultraviolet light having a wavelength shorter than 200 nm so that a carbon-carbon covalent bond is disconnected, the second ultraviolet light having a wavelength longer than that of the first ultraviolet light within a UV-C wavelength range,
the former-stage irradiator irradiates the sample with the ultraviolet light without performing aeration for the sample, and
the intensity of the fluorescence leading to the background noise is lower than the intensity of the autofluorescence of the microviable particle.

2. The microviable particle counting system according to claim 1, wherein
the former-stage irradiator further includes a storage configured to store the sample and a flow passage portion configured to supply the sample in the storage to the microviable particle counting instrument,
the single light source is configured to irradiate the sample in the storage with the ultraviolet light, and
the single light source includes a light emitter configured to emit the ultraviolet light, and irradiates the sample with the ultraviolet light in a state in which an entirety of the light emitter is submerged in the sample in the storage.

3. The microviable particle counting system according to claim 1, wherein
the former-stage irradiator further includes a flow passage portion disposed at a periphery of the single light source such that the sample circulates in the flow passage portion, and a shield configured to cover the single light source and the flow passage portion to reflect or absorb the ultraviolet light.

4. The microviable particle counting system according to claim 3, wherein
the single light source includes a light emitter configured to emit the ultraviolet light, and the flow passage portion is a U-shaped tube extending along a periphery of the light emitter.

5. The microviable particle counting system according to claim 3, wherein
the single light source includes a light emitter configured to emit the ultraviolet light,
the flow passage portion is a cylindrical case, and is configured to house the single light source along a center axis inside the flow passage portion, and
a sample outlet port is, at the flow passage portion, provided at a position identical to or higher than an upper end of the light emitter above a sample inlet port of the flow passage portion.

6. The microviable particle counting system according to claim 5, wherein
the inlet port and the outlet port are provided along a tangential direction of an outer peripheral surface of the flow passage portion.

7. The microviable particle counting system according to claim 1, wherein
the sample is water, and
the microviable particle contains at least one of riboflavin or NAD(P)H.

8. The microviable particle counting system according to claim 1, wherein
the first ultraviolet light has the wavelength shorter than 200 nm so that the carbon-carbon covalent bond and an oxygen molecular bond are disconnected.

9. The microviable particle counting system according to claim 1, wherein the wavelength of the first ultraviolet light is equal to or less than 185 nm.

10. A microviable particle counting method comprising:
irradiating a sample as fluid with ultraviolet light; and
detecting autofluorescence of a microviable particle in the sample irradiated with the ultraviolet light, thereby counting the microviable particle in the sample,
wherein the sample includes a humic substance emitting fluorescence leading to background noise on the autofluorescence of the microviable particle,
the ultraviolet light contains first ultraviolet light and second ultraviolet light, the first ultraviolet light having a wavelength shorter than 200 nm so that a carbon-carbon covalent bond is disconnected, the second ultraviolet light having a wavelength longer than that of the first ultraviolet light within a UV-C wavelength range,
no aeration for the sample is performed during the irradiating the sample, and
the intensity of the fluorescence leading to the background noise is lower than the intensity of the autofluorescence of the microviable particle.

11. The microviable particle counting method according to claim 10, wherein
the first ultraviolet light has the wavelength shorter than 200 nm so that the carbon-carbon covalent bond and an oxygen molecular bond are disconnected.

12. The microviable particle counting method according to claim 10, wherein the wavelength of the first ultraviolet light is equal to or less than 185 nm.

13. A microviable particle counting system comprising:
a microviable particle counting instrument configured to detect autofluorescence of a microviable particle in a sample as fluid, thereby counting the microviable particle in the sample; and
a former-stage irradiator provided at a former stage of the microviable particle counting instrument to irradiate the sample with ultraviolet light, wherein
the ultraviolet light contains first ultraviolet light having such a wavelength that a carbon-carbon covalent bond is disconnected,
the first ultraviolet light has a wavelength shorter than 200 nm,
the former-stage irradiator includes a light source configured to emit the ultraviolet light, a flow passage portion disposed at a periphery of the light source such that the sample circulates in the flow passage portion, and a shield configured to cover the light source and the flow passage portion to reflect or absorb the ultraviolet light,
the light source includes a light emitter configured to emit the ultraviolet light,
the flow passage portion is a cylindrical case, and is configured to house the light source along a center axis inside the flow passage portion, and
a sample outlet port is, at the flow passage portion, provided at a position identical to or higher than an upper end of the light emitter above a sample inlet port of the flow passage portion.

14. The microviable particle counting system according to claim 13, wherein
the inlet port and the outlet port are provided along a tangential direction of an outer peripheral surface of the flow passage portion.

* * * * *